United States Patent
Watanabe et al.

(10) Patent No.: US 8,954,095 B2
(45) Date of Patent: Feb. 10, 2015

(54) MEASUREMENT SYSTEM, MOVING-OBJECT-MOUNTED TERMINAL AND DATA PROCESSING APPARATUS

(75) Inventors: Tsutomu Watanabe, Kawasaki (JP); Tomomi Kageyama, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 450 days.

(21) Appl. No.: 13/312,165

(22) Filed: Dec. 6, 2011

(65) Prior Publication Data

US 2012/0225674 A1    Sep. 6, 2012

(30) Foreign Application Priority Data

Mar. 2, 2011 (JP) ................................. 2011-045738

(51) Int. Cl.
| | |
|---|---|
| *H04W 24/00* | (2009.01) |
| *A61B 5/11* | (2006.01) |
| *A61B 5/00* | (2006.01) |
| *G07C 1/22* | (2006.01) |

(52) U.S. Cl.
CPC ............. *A61B 5/1112* (2013.01); *A61B 5/0002* (2013.01); *G07C 1/22* (2013.01); *A61B 2503/40* (2013.01)
USPC .................................... 455/456.5; 455/456.1

(58) Field of Classification Search
USPC .................. 455/11.1, 456.1, 456.5, 552.1
See application file for complete search history.

(56) References Cited

U.S. PATENT DOCUMENTS

| | | | |
|---|---|---|---|
| 5,642,285 | A | 6/1997 | Woo et al. |
| 7,667,642 | B1 | 2/2010 | Frericks et al. |
| 2002/0198612 | A1 | 12/2002 | Smith et al. |

(Continued)

FOREIGN PATENT DOCUMENTS

| | | |
|---|---|---|
| FR | 2 930 421 A1 | 10/2009 |
| GB | 2 452 538 A | 3/2009 |
| JP | 10-160820 A | 6/1998 |

(Continued)

OTHER PUBLICATIONS

Akira Kuriyama, "Trained Horse Automatic Measurement System", Business Structure of Sumitomo Metal Technology, Inc., Nov. 19, 2010, 2 pages with English Translation.

(Continued)

*Primary Examiner* — Sam Bhattacharya
(74) *Attorney, Agent, or Firm* — Oblon, Spivak, McClelland, Maier & Neustadt, L.L.P.

(57) ABSTRACT

According to one embodiment, a measurement system includes a wireless relay device, a moving-object-mounted terminal and a data processor. The wireless relay device forms a wireless area for performing wireless communication. The moving-object-mounted terminal is mounted to a moving object within the wireless area. The moving-object-mounted terminal includes a Global Positioning System (GPS) unit and a wireless unit. The GPS unit acquires positional data of the moving object and time data indicating the time when the positional data has been acquired by GPS. The wireless unit converts the positional data and the time data into a wireless signal, and transmits the wireless signal to the wireless relay device. The data processor receives the wireless signal from the moving-object-mounted terminal via the wireless relay device, and calculates time required for the moving object to move a predetermined distance within the wireless area based on the positional data and the time data.

38 Claims, 10 Drawing Sheets

(56) References Cited

U.S. PATENT DOCUMENTS

2008/0036587 A1    2/2008    Meinzen et al.
2011/0320112 A1*    12/2011    Anderson .................... 701/119

FOREIGN PATENT DOCUMENTS

| | | |
|---|---|---|
| JP | 10-304351 A | 11/1998 |
| JP | 11-149599 A | 6/1999 |
| JP | 2000-48283 A | 2/2000 |
| JP | 2002-156435 A | 5/2002 |
| JP | 2002-222498 A | 8/2002 |
| JP | 2002-277525 A | 9/2002 |
| JP | 2003-296493 | 10/2003 |
| JP | 2005-80635 A | 3/2005 |
| JP | 2006-523092 A | 10/2006 |
| JP | 2008-500046 A | 1/2008 |
| JP | 2009-25045 A | 2/2009 |
| JP | 2009-517047 A | 4/2009 |
| JP | 2011-85475 | 4/2011 |
| JP | 2011-97874 A | 5/2011 |
| JP | 2011-522569 A | 8/2011 |
| WO | WO 2004/084624 A1 | 10/2004 |
| WO | WO 2010/140620 A1 | 12/2010 |

OTHER PUBLICATIONS

Extended European Search Report issued Nov. 7, 2012 in Patent Application No. 11191620.1.

Australian Office Action Issued Apr. 9, 2013 in Patent Application No. 2011253838.

Office Action issued on May 7, 2014 in the corresponding Japanese patent Application No. 2011-045738 (with English Translation).

European Search Report dated Sep. 5, 2014 issued in European Patent Application No. 11 191 620.1 (in English).

Pizzarulli, A. et al., "Reconfigurable and Simultaneous Dual Band Galileo/GPS Front-end Receiver in 0.13μm RFCMOS", May 5, 2008, pp. 846-850.

* cited by examiner

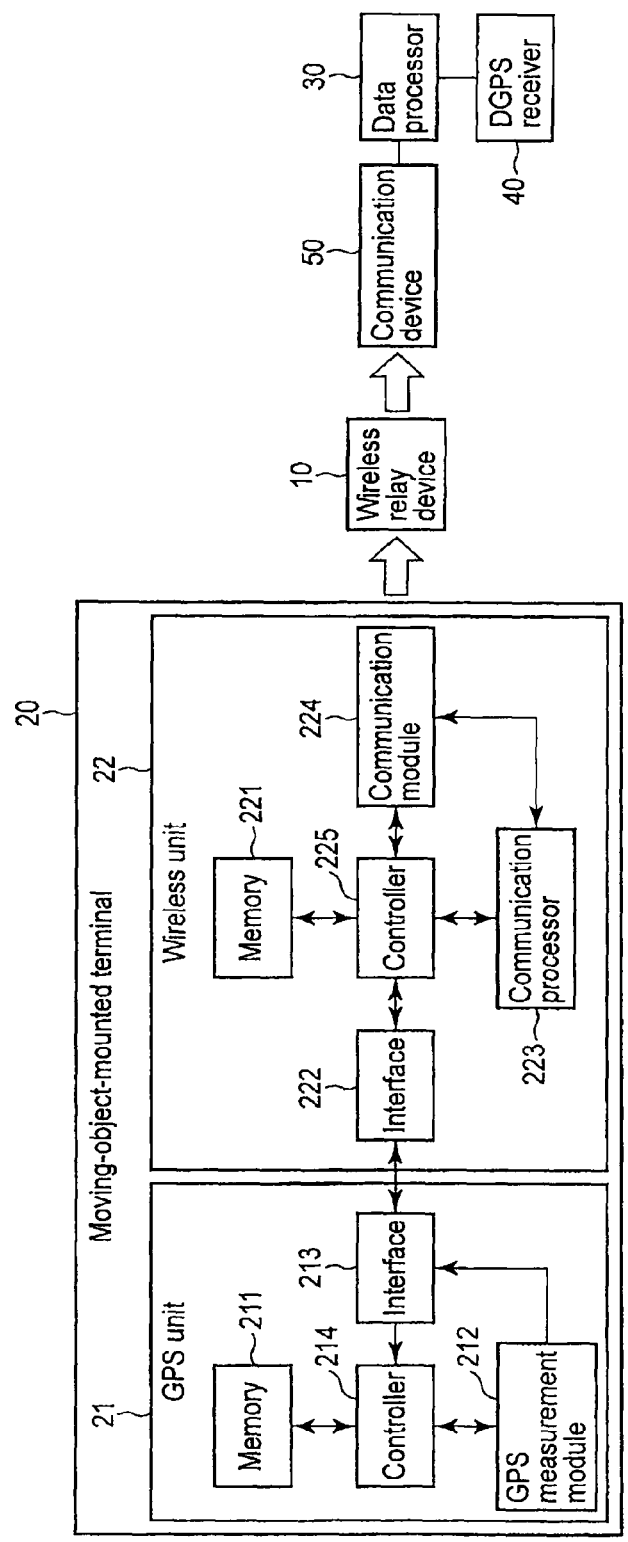
F I G. 1

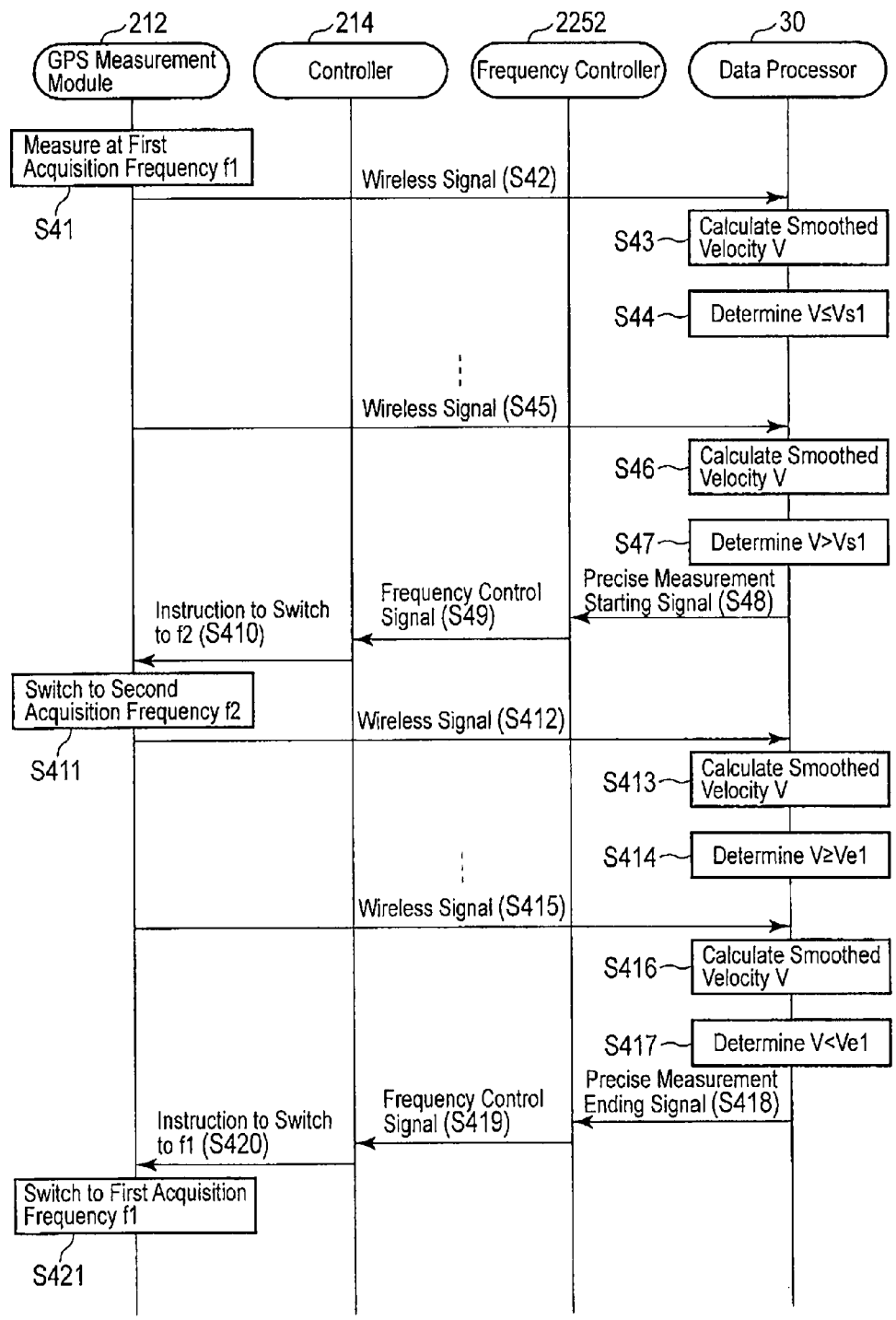
F I G. 4

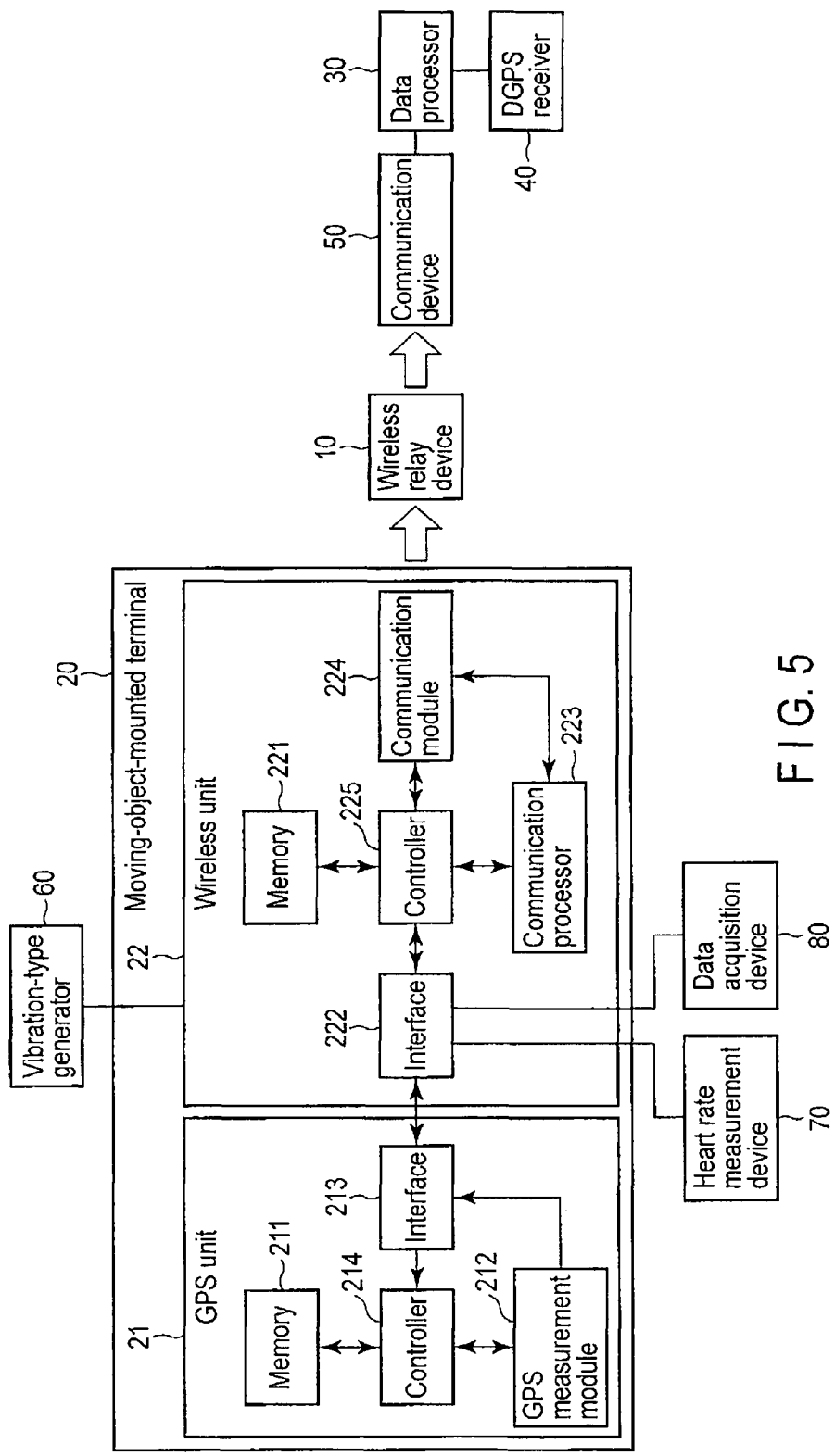
F I G. 5

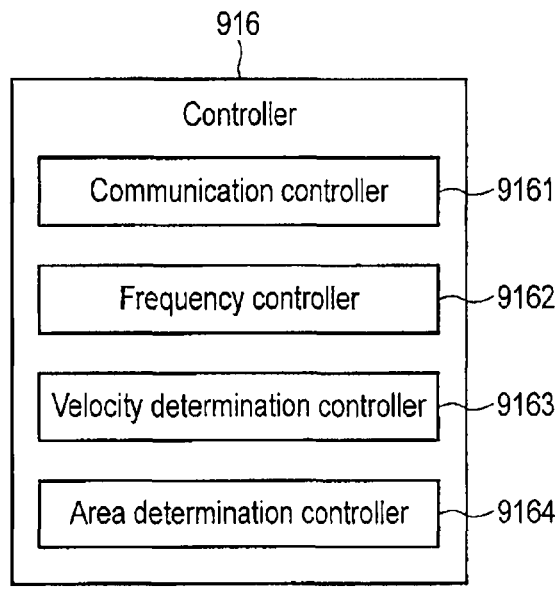
F I G. 7
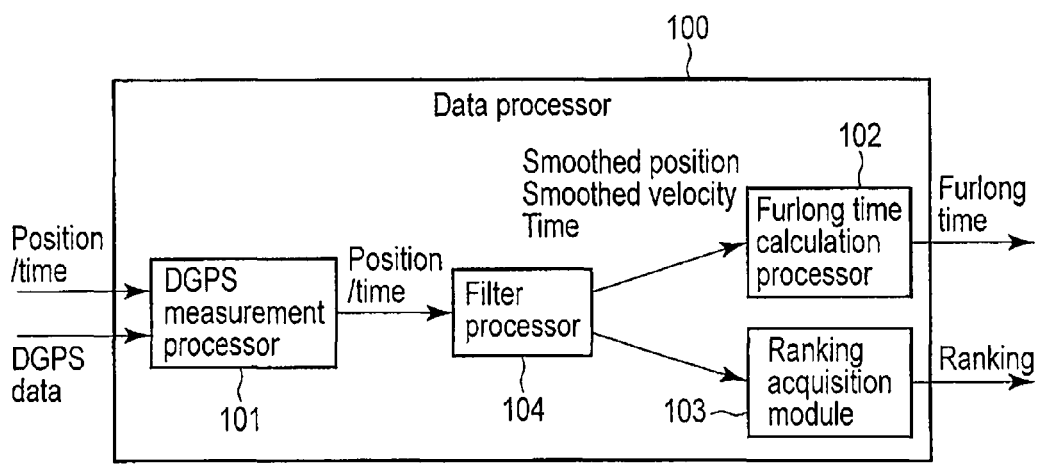
F I G. 8

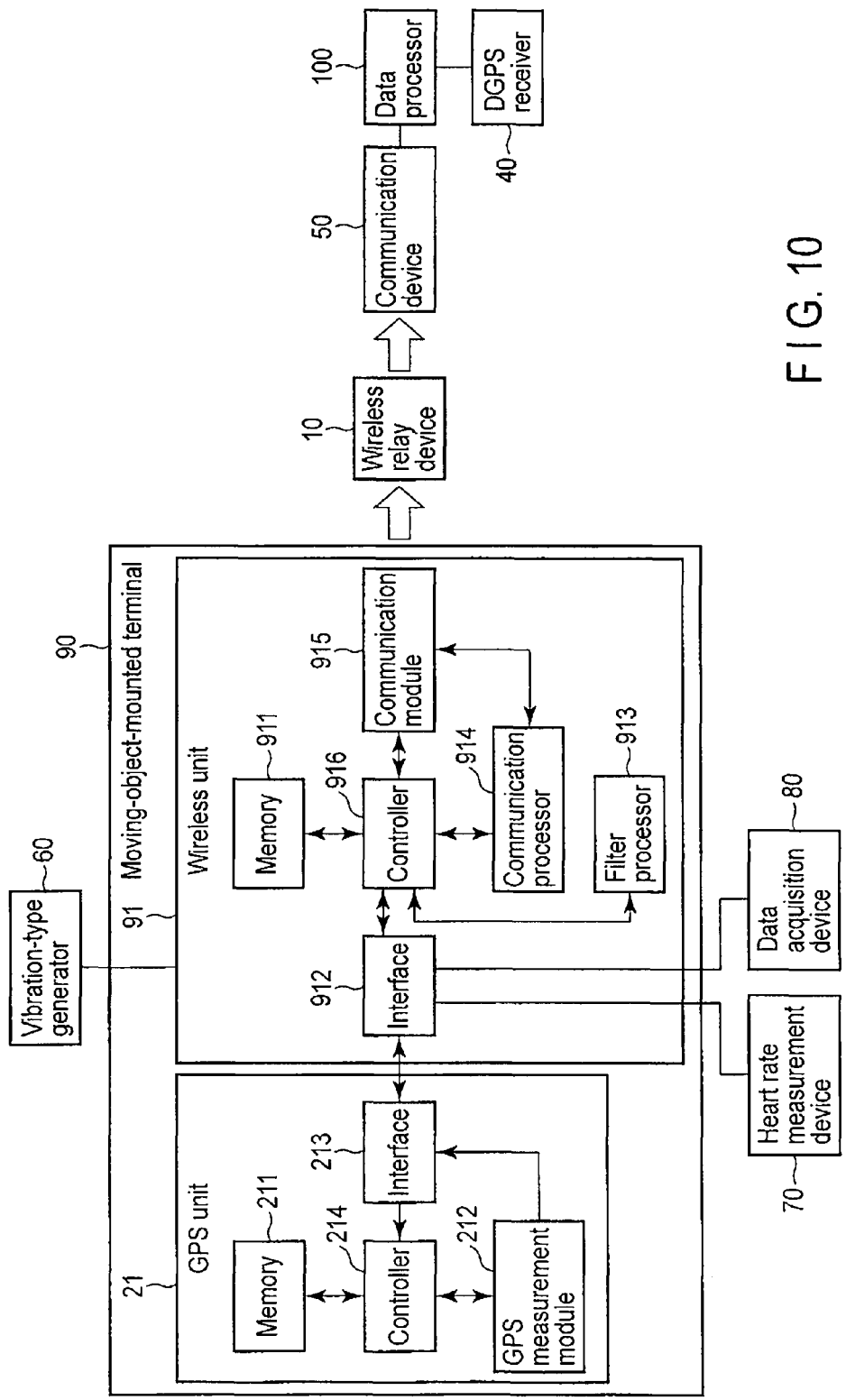
F I G. 10

| Smoothed velocity V | Transmission | Acquisition frequency |
|---|---|---|
| $V \leq V_{S0}$ | OFF | $f_0$ |
| $V_{S0} < V \leq V_{S1}$ | ON | $f_1$ |
| $V_{S1} < V$ | ON | $f_2$ |
F I G. 11
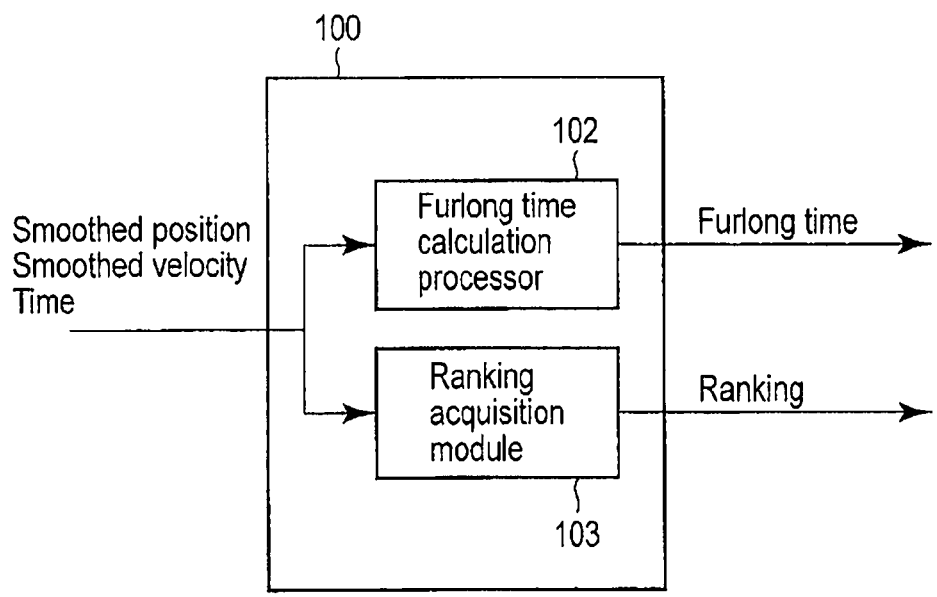
F I G. 13

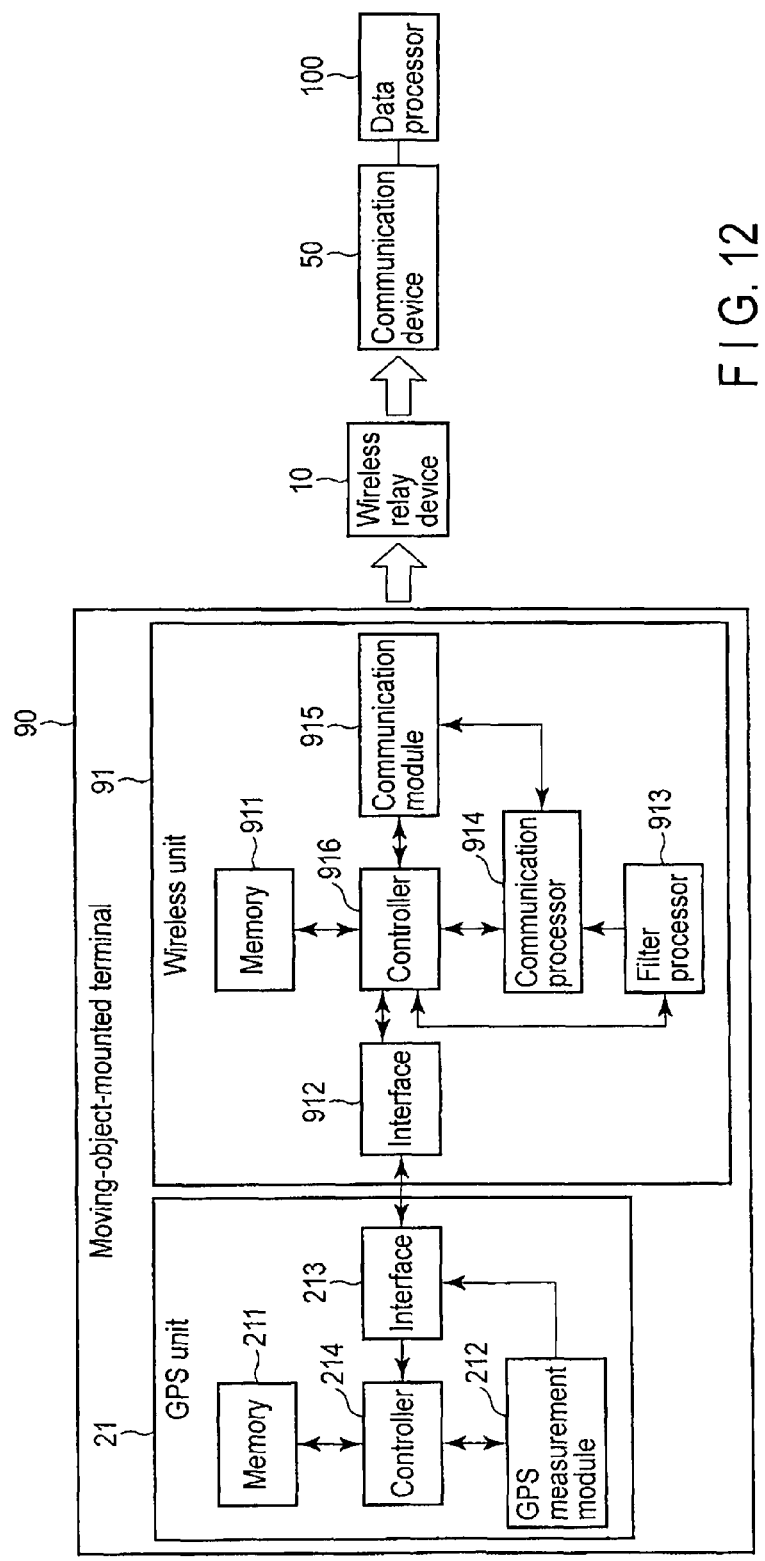
F I G. 12

MEASUREMENT SYSTEM, MOVING-OBJECT-MOUNTED TERMINAL AND DATA PROCESSING APPARATUS

CROSS-REFERENCE TO RELATED APPLICATIONS

This application is based upon and claims the benefit of priority from prior Japanese Patent Application No. 2011-045738, filed Mar. 2, 2011, the entire contents of which are incorporated herein by reference.

FIELD

Embodiments described herein relate generally to a measurement system, a moving-object-mounted terminal and a data processing apparatus.

BACKGROUND

For racehorse training, furlong time which is a split time measured for each furlong (a furlong is approximately equal to 200 m) is used. The furlong time is effective to understand the current ability and training result of a racehorse and to perform appropriate training. Some of large training centers for racehorses have adopted a system for automatically obtaining furlong time data (Advanced Lap time Information System: ALIS). ALIS should surely obtain the furlong time for a racehorse galloping at speed and should be not noticed in the sense of frightening the racehorses.

For example, for the conventional ALIS, a barcode is attached to a racehorse, and barcode readers are placed for each furlong (at 200 m intervals). The furlong time is obtained by measuring times when the racehorse crossing each furlong.

For such the conventional ALIS, large-sized gates for which the barcode readers are placed are necessary so that racehorses do not notice the ALIS. In such a case, since the barcode readers are placed separately from the barcodes attached to racehorses, a problem that the furlong time of a fast racehorse cannot be accurately obtained may occur.

In addition, it is very costly to place large-sized gates, and the cost for maintenance will also be large since the barcode readers of the gates are placed in elevated areas.

BRIEF DESCRIPTION OF THE DRAWINGS

FIG. 1 is an exemplary block diagram showing a configuration of a measurement system according to the first embodiment.

FIG. 4 illustrates the sequence of switching acquisition frequencies of the GPS measurement module of the measurement system shown in FIG. 1.

FIG. 5 is an exemplary block diagram showing another configuration of the measurement system shown in FIG. 1.

FIG. 7 is an exemplary block diagram showing a configuration of the controller shown in FIG. 6.

FIG. 8 is an exemplary block diagram showing a configuration of the data processor shown in FIG. 6.

FIG. 10 is an exemplary block diagram showing another configuration of the measurement system shown in FIG. 6.

FIG. 11 illustrates the operation of the moving-object-mounted terminal shown in FIG. 6.

FIG. 12 is an exemplary block diagram showing another configuration of the measurement system shown in FIG. 6.

FIG. 13 is an exemplary block diagram showing a configuration of the data processor shown in FIG. 12.

DETAILED DESCRIPTION

Figure 2:
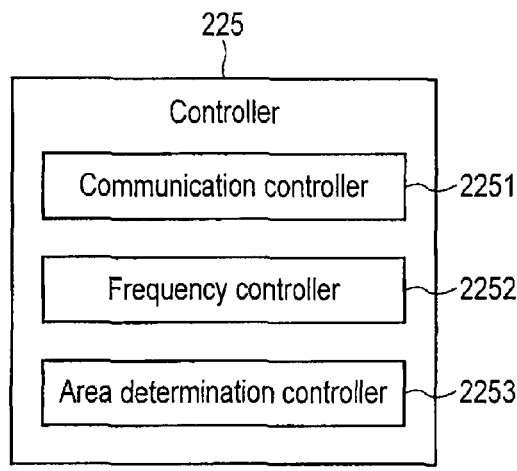
FIG. 2 is an exemplary block diagram showing a configuration of the controller shown in FIG. 1.

In general, according to one embodiment, a measurement system includes a wireless relay device, a moving-object-mounted terminal and a data processor. The wireless relay device forms a wireless area for performing wireless communication. The moving-object-mounted terminal is mounted to a moving object within the wireless area. The moving-object-mounted terminal includes a Global Positioning System (GPS) unit and a wireless unit. The GPS unit acquires positional data of the moving object and time data indicating the time when the positional data has been acquired by GPS. The wireless unit converts the positional data and the time data into a wireless signal, and transmits the wireless signal to the wireless relay device. The data processor receives the wireless signal from the moving-object-mounted terminal via the wireless relay device, and calculates time required for the moving object to move a predetermined distance within the wireless area based on the positional data and the time data.

First Embodiment

In the following, the present embodiment will be described in details with reference to the drawings.

FIG. 1 is a block diagram showing a configuration of a measurement system according to the first embodiment. The measurement system shown in FIG. 1 includes a wireless relay device 10, a moving-object-mounted terminal 20, a data processor 30, a Differential Global Positioning System (DGPS) receiver 40 and a communication device 50. This embodiment will illustrate an example of measuring the span of time that a racehorse has galloped over a predetermined distance. In the following, the predetermined distance is one furlong (about 200 m), and the span of time that a racehorse has galloped over a furlong is called furlong time.

The wireless relay device 10 is, for example, a wireless LAN relay device which complies with IEEE 802.11a/b/g, and forms a wireless area in which wireless communication is available. One or more wireless relay devices 10 are provided so that the whole measurement course for measuring furlong time is included in the wireless area.

The moving-object-mounted terminal 20 is mounted to a moving object within the wireless area. Although FIG. 1 merely shows one moving-object-mounted terminal 20, there is a case where multiple moving-object-mounted terminals 20 exist within the wireless area since the moving-object-mounted terminal 20 are attached to each moving object within the wireless area. In this embodiment, the moving object means a combination of a racehorse and a rider, and the moving-object-mounted terminal may be attached to either the racehorse or the rider.

The moving-object-mounted terminal 20 includes a Global Positioning System (GPS) unit 21 and a wireless unit 22.

The GPS unit 21 includes a memory 211, a GPS measurement module 212, an interface 213 and a controller 214.

The memory 211 stores a first acquisition frequency f1 and a second acquisition frequency f2 beforehand, where f1<f2.

The GPS measurement module 212 receives radio waves from a plurality of artificial satellites and measures current positional coordinates of the moving object. The GPS measurement module 212 acquires positional data of the moving object in one of the first and second acquisition frequencies f1, f2 stored in the memory 211 in accordance with an instruction from the controller 212. The GPS measurement module 212 then outputs the acquired positional data and time data indicating the time when the positional data has been acquired to the wireless unit 22 via the interface 213.

The interface 213 is an interface between the GPS unit 21 and the wireless unit 22. The interface 213 outputs the positional data and the time data obtained from the GPS measurement module 212 to the wireless unit 22. The interface 213 also outputs a signal received from the wireless unit 22 to the controller 214.

The controller 214 provides an instruction to the GPS measurement module 212 to acquire positional data of the moving object in accordance with one of the first and second acquisition frequencies on the basis of a frequency control signal output from the wireless unit 22. The frequency control signal will be explained later.

The wireless unit 22 includes a memory 221, an interface 222, a communication processor 223, a communication module 224 and a controller 225.

The memory 221 stores an identification (ID) number assigned to the moving-object-mounted terminal 20 beforehand. The memory 221 also stores area data of a measurement area and individual information of the moving object beforehand. The individual information includes the name of horse, and a unique number assigned for each racehorse, for example.

The interface 222 receives the positional data and the time data from the GPS unit 21. The interface 222 also outputs the frequency control signal received from the controller 225 to the GPS unit 21.

The communication processor 223 receives the positional data and the time data from the GPS unit 21 and the ID number and the individual information from the memory 221, and modulates the received data according to the communication format. The communication processor 223 outputs the modulated signal to the communication module 224.

The communication processor 223 demodulates the wireless signal received at the communication module 224 according to the communication format. The communication processor 223 then outputs the demodulated signal to the controller 225.

The communication module 224 up-converts the frequency of the modulated signal received from the communication processor 223 to the frequency band for wireless communication, power-amplifies the signal, and externally transmits the signal as a wireless signal. If the positional data and the time data are acquired at the first acquisition frequency f1, the communication module 224 may transmit the wireless signal at a transmit frequency which is less than or equal to f1. If the positional data and the time data are acquired at the second acquisition frequency f2, the communication module 224 may transmit the wireless signal at a transmit frequency which is less than or equal to f2. If the wireless signal is transmitted at a transmit frequency lower than f1 or f2, the positional data and the time data are temporally stored in the memory 221.

The communication module 224 receives the externally transmitted wireless signal. The communication module 224 also transfers the frequency of the received wireless signal to an intermediate frequency band and outputs the signal to the communication processor 223.

The communication module 224 is turned on or off by the controller 225.

The controller 225 includes a central processing unit (CPU), for example, and has functions as shown in FIG. 2. The controller 225 includes a communication controller 2251, a frequency controller 2252 and an area determination controller 2253.

When the positional data and the time data are input from the GPS unit 21 to the communication controller 2251 via the interface 222, the communication controller 2251 reads the ID number and the individual information from the memory 221 and outputs the ID number and the individual information along with the positional data and the time data received from the GPS unit 21 to the communication processor 223.

The frequency controller 2252 receives the demodulated signal from the communication processor 223 and determines whether the demodulated signal includes an instruction of starting precise measurement or an instruction of ending precise measurement, which will be explained later. If the received demodulated signal includes the instruction of starting precise measurement, the frequency controller 2252 outputs a frequency control signal to cause the GPS unit 21 to execute GPS measurement at the second acquisition frequency f2. If the received demodulated signal includes the instruction of ending precise measurement, the frequency controller 2252 outputs a frequency control signal to cause the GPS unit 21 to execute GPS measurement at the first acquisition frequency f1.

The area determination controller 2253 compares the positional data received from GPS unit 21 with area data stored in the memory 221 and determines whether the moving object exists within the measurement area upon reception of the positional data. If the moving object does not exists within the measurement area, the area determination controller 2253 turns off the communication module 224 not to transmit or receive the wireless signal. If the moving object exists within the measurement area, the area determination controller 2253 turns on the communication module 224 to transmit or receive the wireless signal.

The communication device 50 shown in FIG. 1 receives the wireless signal from the moving-object-mounted terminal 20 via the wireless relay device 10. The communication device 50 transforms the wireless signal received from the moving-object-mounted terminal 20 to an IF signal in the intermediate frequency band, and demodulates the IF signal in accordance with the communication format. The communication device 50 outputs the demodulated signal to the data processor 30. The demodulation signal includes the positional data, the time data, the ID number and the individual information.

Figure 3:
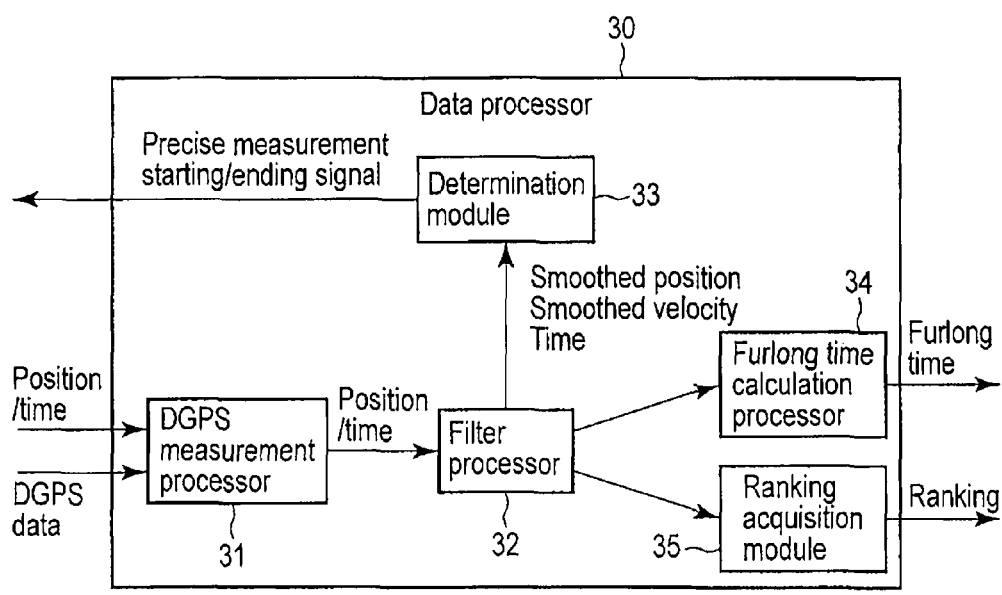
FIG. 3 is an exemplary block diagram showing a configuration of the data processor shown in FIG. 1.

The data processor 30 receives DGPS data acquired by the DGPS receiver 40 and the demodulated signal from the communication device 50. FIG. 3 is a block diagram showing the configuration of the data processor 30 according to the first embodiment. The data processor 30 shown in FIG. 3 includes a DGPS measurement processor 31, a filter processor 32, a determination module 33, a furlong time calculation processor 34 and a ranking acquisition module 35.

The DGPS measurement processor 31 performs DGPS processing by using the positional data and the time data included in the demodulated signal and the DGPS data received from the DGPS receiver 40. The DGPS processing is position correction processing which includes calculating an error component from the positional data received from the DGPS receiver 40 fixed to a predetermined position whose precise position is acquired, and eliminate the error component included in the positional data acquired from the moving-object-mounted terminal 20 based on the correlation between the positional data acquired from the fixed DGPS receiver and moving-object-mounted terminal 20. The observational error which is a random component is added to the positional data after the DGPS processing. The DGPS measurement processor 31 outputs the positional data subjected to the DGPS processing and the time data to the filter processor 32.

The filter processor 32 performs filter processing on the time-sampled series of positional data. By this processing, the filter processor 32 calculates the positional data in which the observation error is reduced (hereinafter, referred to as smoothed position) and the smoothed rate of movement (hereinafter, referred to as smoothed velocity). The filter processor 32 outputs the calculated smoothed velocity to the determination module 33. The filter processor 32 also outputs the calculated smoothed position, smoothed velocity and time data to the furlong time calculation processor 34 and the ranking acquisition module 35.

The filter processing is one of the techniques used for a radar tracking a target. For example, the α-β filter and the Kalman filter have been widely used. The α-β filter calculates a predicted value of the target and a smoothed value in which the observation error is reduced by sequentially calculating the target velocity from the observed target location. The Kalman filter produces a predicted value or a smoothed value from the observed value by setting a motion model of the target such as linear uniform motion and uniform acceleration motion.

An example of calculation method of filtering with a light calculation load will be explained below. Generally, the filter factors (α, β) perform optimization in accordance with the observation number N and the observation error. In the equation indicated below, $X_{mN}$ represents an observed location, $X_{SN}$ represents a smoothed location, $X'_{SN}$ represents a smoothed velocity, $X_{PN}$ represents a predicted location, and $T_N$ represents observation time.

Where N=0,
$X_{S0}=X_{m0}$
$X'_{S0}=0$
$X_{p1}=X_{S0}$
Where N≥1,
$X_{SN}=X_{pN}+\alpha_N(X_{mN}-X_{pN})$
$X'_{SN}=X'_{SN-1}+\beta_N(X_{mN}-X_{pN})/(T_N-T_{N-1})$
$X_{pN+1}=X_{SN-1}+X'_{SN}(T_{N+1}-T_N)$
Where N≥K (K is sufficiently large value so that the smoothed location and the smoothed velocity is stable.)
start velocity determination by $X'_{SN}$ The precise measurement starting velocity $V_{s1}$ and the precise measurement ending velocity $V_{e1}$ are preset in the determination module 33, where $V_{s1} \geq V_{e1}$. The determination module 33 receives the smoothed velocity from the filter processor 32. The received smoothed velocity includes the ID number. The determination module 33 compares the smoothed velocity with the precise measurement starting velocity $V_{s1}$ and the precise measurement ending velocity $V_{e1}$. If the smoothed velocity > $V_{s1}$, the determination module 33 generates a precise measurement starting signal to the moving-object-mounted terminal 20 which is identified by the ID number. The precise measurement starting signal is modulated at the communication device 50, and transmitted to the moving-object-mounted terminal 20 as a wireless signal via the wireless relay device 10.

If the smoothed velocity < $V_{e1}$, the determination module 33 generates a precise measurement ending signal to the moving-object-mounted terminal 20 which is identified by the ID number. The precise measurement ending signal is modulated at the communication device 50, and transmitted to the moving-object-mounted terminal 20 as a wireless signal via the wireless relay device 10.

The furlong time calculation processor 34 receives the smoothed velocity, smoothed position and time data from the filter processor 32. The received smoothed velocity, smoothed location and time data include the ID number and individual information. The furlong time calculation processor 34 calculates time when the moving object passes through the preset start position and finish position of each furlong on the basis of the smoothed velocity, smoothed position and time data, and calculates the time difference as a furlong time. The furlong time calculation processor 34 calculates furlong times for each moving object identified by the ID number, and outputs the calculated furlong times, the ID number and the individual information to the post-processing format.

The ranking acquisition module 35 receives the smoothed velocity, smoothed position and time data from the filter processor 32. The ranking acquisition module 35 acquires the ranking of moving objects at the time when they passed through the preset positions within the wireless area, on the basis of the smoothed velocity, smoothed position, time data and ID numbers. The ranking acquisition module 35 outputs the acquired ranking, ID numbers and individual information to the post-processing format.

For example, the post-processing format may be a display (not shown), and the furlong time and the ranking associated with the ID number and individual information may be shown on the display.

The operation of switching the acquiring frequencies by the GPS unit 21 in the above-mentioned measurement system will be described below in the details.

FIG. 4 illustrates an example sequence of switching acquisition frequencies by the GPS measurement module 212 of the measurement system according to the first embodiment.

The wireless area includes one or more measurement courses. If a racehorse enters the wireless area, wireless communication between the wireless unit 22 and wireless relay device 10 is established. At the time when the wireless communication is established, an instruction for initiating GPS measurement is provided to the GPS unit 21 so that the GPS measurement module 212 starts GPS measurement by the controller 225. The GPS measurement module 212 acquires the positional data and time data at the first acquisition frequency f1 (sequence S41). The acquired positional data and time data are converted into a wireless signal to be transmitted to the data processor 30 via the wireless relay device 10 (sequence S42).

The data processor 30 calculates the smoothed velocity V based on the positional data and time data included in the received wireless signal (sequence S43). The data processor 30 compares the smoothed velocity V with the precise measurement starting velocity $V_{s1}$ and the precise measurement ending velocity $V_{e1}$ by means of the determination module 33 (sequence S44). Until the determination module 33 determines that V>$V_{s1}$, the GPS unit 21 continuously acquires the positional data and time data at the first acquisition frequency f1 and transmits the wireless signal obtained by converting the positional data and time data (sequence S45).

If the smoothed velocity V calculated at the data processor 30 becomes greater than $V_{s1}$ (V>$V_{s1}$) (sequences S46, S47), the data processor 30 transmits a precise measurement starting signal to the corresponding moving-object-mounted terminal 20 (sequence S48).

The frequency controller 2252 outputs a frequency control signal instructing initiation of GPS measurement at the second acquisition frequency f2 to the GPS unit 21 upon reception of the precise measurement starting signal from the data processor 30 (sequence S49). The controller 214 reads the second acquisition frequency f2 from the memory 211 and controls the GPS measurement module 212 to initiate GPS measurement at the second acquisition frequency f2 upon reception of the frequency control signal from the frequency controller 2252 (sequence S410).

The GPS measurement module 212 performs the GPS measurement at the second acquisition frequency f2 and acquires the positional data and time data (sequence S411). The acquired positional data and time data are converted into a wireless signal and transmitted to the data processor 30 via the wireless relay device 10 (sequence S412).

The data processor 30 calculates the smoothed velocity V based on the positional data and time data included in the received wireless signal (sequence S413). The data processor 30 compares the smoothed velocity V with the precise measurement starting velocity $V_{s1}$ and the precise measurement ending velocity $V_{e1}$ by means of the determination module 33 (sequence S414). Until the determination module 33 determines that $V<V_{e1}$, the GPS unit 21 continuously acquires the positional data and time data at the second acquisition frequency f2 and transmits the wireless signal obtained by converting the positional data and time data (sequence S415).

If the smoothed velocity V calculated at the data processor 30 becomes less than $V_{e1}$ ($V<V_{e1}$) (sequences S416, S417), the data processor 30 transmits a precise measurement ending signal to the corresponding moving-object-mounted terminal 20 (sequence S418).

The frequency controller 2252 outputs a frequency control signal instructing initiation of GPS measurement at the first acquisition frequency f1 to the GPS unit 21 upon reception of the precise measurement ending signal from the data processor 30 (sequence S419). The controller 214 reads the first acquisition frequency f1 from the memory 211 and controls the GPS measurement module 212 to initiate GPS measurement at the first acquisition frequency f1 upon reception of the frequency control signal from the frequency controller 2252 (sequence S420).

The GPS measurement module 212 performs the GPS measurement at the first acquisition frequency f1 and acquires the positional data and time data (sequence S421).

In the first embodiment, the wireless area including the measurement area is formed by the wireless relay device 10, and the moving-object-mounted terminal 20 transmits the positional data and time data acquired by the GPS measurement to the data processor 30 via the wireless LAN. Accordingly, it is possible not to frighten racehorses without a large-sized gate and to realize transmission of the positional data and time data of racehorses to the data processor 30.

According to the first embodiment, the frequency of GPS measurement by the GPS unit 21 is changed in accordance with the smoothed velocity of a racehorse. This accomplishes high-precision furlong time measurement by increasing the acquisition frequency when a racehorse moves at high velocity (greater than or equal to $V_{s1}$).

According to the first embodiment, the data processor 30 performs the filter processing on the positional data and time data received from the moving-object-mounted terminal 20. This realizes calculation of the smoothed velocity and smoothed position even if the GPS measurement is performed in the different acquisition frequencies. In addition, the smoothed velocity and smoothed position can be calculated even if the GPS data cannot be continuously received due to the low data communication quality in the wireless LAN communication.

According to the first embodiment, if a position indicated by the positional data acquired by the GPS measurement is not included in the measurement area defined by the pre-stored area data, the communication module 224 is turned off by the area determination controller 2253, thus reducing power requirements. In addition, if the position indicated by the positional data acquired by the GPS measurement is not include in the measurement area defined by the pre-stored area data, the frequency control signal output from the controller 225 of the wireless unit 22 is set to fix the frequency of GPS measurement to f1 regardless of the smoothed velocity. This also reduces power requirements.

According to the first embodiment, the ID number of each moving object is pre-stored in the memory 221 of the wireless unit 22, thereby identifying each of the plurality of moving-object-mounted terminals 20 in the wireless area.

According to the first embodiment, the individual information of each moving object is pre-stored in the memory 221 of the wireless unit 22, thereby displaying the individual information of each racehorse associated with the calculated furlong times.

As stated above, with the measurement system according to the first embodiment, the furlong time of a racehorse galloping at high velocity can be automatically and surely obtained so that racehorses are not aware of the system even without the presence of a large-sized gate.

The configuration of the measurement system according to the first embodiment may not be limited to the configuration shown in FIG. 1. For example, as shown in FIG. 5, the measurement system may further include a vibration-type generator 60.

The vibration-type generator 60 is attached to a racehorse and is connected to the moving-object-mounted terminal 20. The vibration-type generator 60 generates energy by vertical and horizontal vibration as result of the racehorse's gait. The vibration-type generator 60 supplies the generated energy to the moving-object-mounted terminal 20. The GPS unit 21 and the wireless unit 22 are driven by the energy supplied from the vibration-type generator 60. By using the vibration-type generator 60, the frequency of a maintenance of the moving-object-mounted terminal 20, for example charging the moving-object-mounted terminal 20, can be decreased.

As shown in FIG. 5, a heart rate measurement device 70 may be attached to a racehorse. The heart rate measurement device 70 outputs data on heart rate to the wireless unit 22 by a cable communication or a wireless communication such as Bluetooth (registered trademark). The wireless unit 22 converts the heart rate data into a wireless signal together with the positional data and time data, and outputs the signal to the data processor 30 via the wireless relay device 10. The data processor 30 calculates correlation between the stored smoothed velocity and the heart rate to automatically calculate the performance index such as V200 (the velocity at which the heart rate reaches 200 beats per minute [BPM]). The data on V200 is used for evaluating the cardiopulmonary ability of a racehorse. V200 can be easily measured by providing the heart rate measurement device 70, and continuous measurement of V200 is effective to evaluate the effect of training.

A data acquisition device 80 may also be attached to a racehorse as shown in FIG. 5. The data acquisition device 80 may be a camera, a microphone, an acceleration sensor, a pressure sensor or a temperature sensor.

If a camera is attached to a racehorse as an example of the data acquisition device 80, the camera is driven when the precise measurement of position is started, and the obtained video data is transmitted as a wireless signal. Providing the camera realizes automatic acquisition of a dynamic video of moving racehorse.

If a microphone is attached to a racehorse as an example of the data acquisition device 80, the microphone is driven when the precise measurement of position is started, and the obtained audio data is transmitted as a wireless signal. Providing the microphone realizes automatic acquisition of lifelike sound.

If an acceleration sensor is attached to a racehorse as an example of the data acquisition device 80, variation of output from the acceleration sensor due to the horse's gait can be obtained. Accordingly, a stride can be calculated from the moving distance obtained from the GPS data and the output of the acceleration sensor.

If a pressure sensor is attached to a hoof of the racehorse as an example of the data acquisition device 80, the relations between the pressure applied to the hoof, the condition of the racecourse and the velocity can be obtained.

According to the first embodiment, the frequency controller 2252 outputs the frequency control signal to switch between the first and second acquisition frequencies f1 and f2 to the GPS unit 21, in accordance with an instruction of starting or ending precise measurement transmitted via the wireless relay device 10. However, the acquisition frequency may be switched in other ways. For example, the frequency control signal to switch between the first and second acquisition frequencies f1 and f2 may be output to the GPS unit 21 on the basis of the positional data transmitted from the GPS unit 21. In a case where the frequency controller 2252 includes both function of controlling the acquisition frequency in accordance with the instruction of starting or ending precise measurement and function of controlling the acquisition frequency in accordance with the position of a moving object, the precise measurement is started if the instruction of starting precise measurement is received, and the positional data indicates a position within a predetermined area, for example.

If the frequency control signal to switch between the first and second acquisition frequencies f1 and f2 is output to the GPS unit 21 on the basis of the positional data, the frequency controller 2252 performs, for example, first or second processing described below.

Below are operations included in the first processing. The frequency controller 2252 compares the positional data with the area data stored in the memory 221 and determines whether the moving object is within the measurement area upon reception of the positional data from the GPS unit 21. If the moving object is not within the measurement area, the frequency controller 2252 outputs a frequency control signal indicating execution of GPS measurement at the first acquisition frequency f1 to the GPS unit 21. If the moving object is within the measurement area, the frequency controller 2252 outputs a frequency control signal indicating execution of GPS measurement at the second acquisition frequency f2 to the GPS unit 21.

Below are operations included in the second processing. The memory 221 pre-stores first and second area data. The first area data is used for turning on or off the communication module 224 by the area determination controller 2253. The second area data refers to a part of the first area data.

If the frequency controller 2252 receives the positional data from the GPS unit 21, the frequency controller 2252 compares the received positional data with the second area data stored in the memory 221 and determines whether the moving object is within the area defined by the second area data. If the moving object is within the area defined by the second area data, the frequency controller 2252 outputs a frequency control signal instructing execution of GPS measurement at the first acquisition frequency f1 to the GPS unit 21. If the moving object is within the area defined by the second area data, the frequency controller 2252 outputs a frequency control signal indicating execution of GPS measurement at the second acquisition frequency f2 to the GPS unit 21.

The first embodiment illustrates an example case where the determination module 33 compares the smoothed velocity obtained from the filter processor 32 with the precise measurement starting velocity $V_{s1}$ and the precise measurement ending velocity $V_{e1}$, and generates a precise measurement starting signal or a precise measurement ending signal. However, the precise measurement starting or ending signal may be generated in other ways. For example, the precise measurement starting or ending signal may be generated based on the smoothed position obtained from the filter processor 32. In a case where the determination module 33 includes both function of generating a precise measurement starting or ending signal based on the velocity and function of generating a precise measurement starting or ending signal based on the position, a precise measurement starting or ending signal is generated if the smoothed velocity exceeds precise measurement starting velocity $V_{s1}$, and the smoothed position is within the predetermined area.

If the precise measurement starting or ending signal is generated based on the smoothed position, the determination module 33 performs, for example, first or second processing described below.

Below are operations included in the first processing. The determination module 33 compares the smoothed position and the preset area data and determines whether the moving object is within the measurement area upon reception of the smoothed position obtained from the filter processor 32. If the smoothed position is not within the area defined by the area data, the determination module 33 generates a precise measurement ending signal. If the smoothed position is within the area defined by the area data, the determination module 33 generates a precise measurement starting signal.

Below are operations included in the second processing. The determination module 33 pre-stores first and second area data. The first area data refers to an area including the measurement area, and the second area data refers to a part of the first area data.

If the determination module 33 receives the smoothed position from the filter processor 32, the determination module 33 compares the received smoothed position with the second area data and determines whether the moving object is within the area defined by the second area data. If the smoothed position is not within the area defined by the second area data, the determination module 33 generates a precise measurement ending signal. If the smoothed position is within the area defined by the second area data, the determination module 33 generates a precise measurement starting signal.

Second Embodiment

Figure 6:
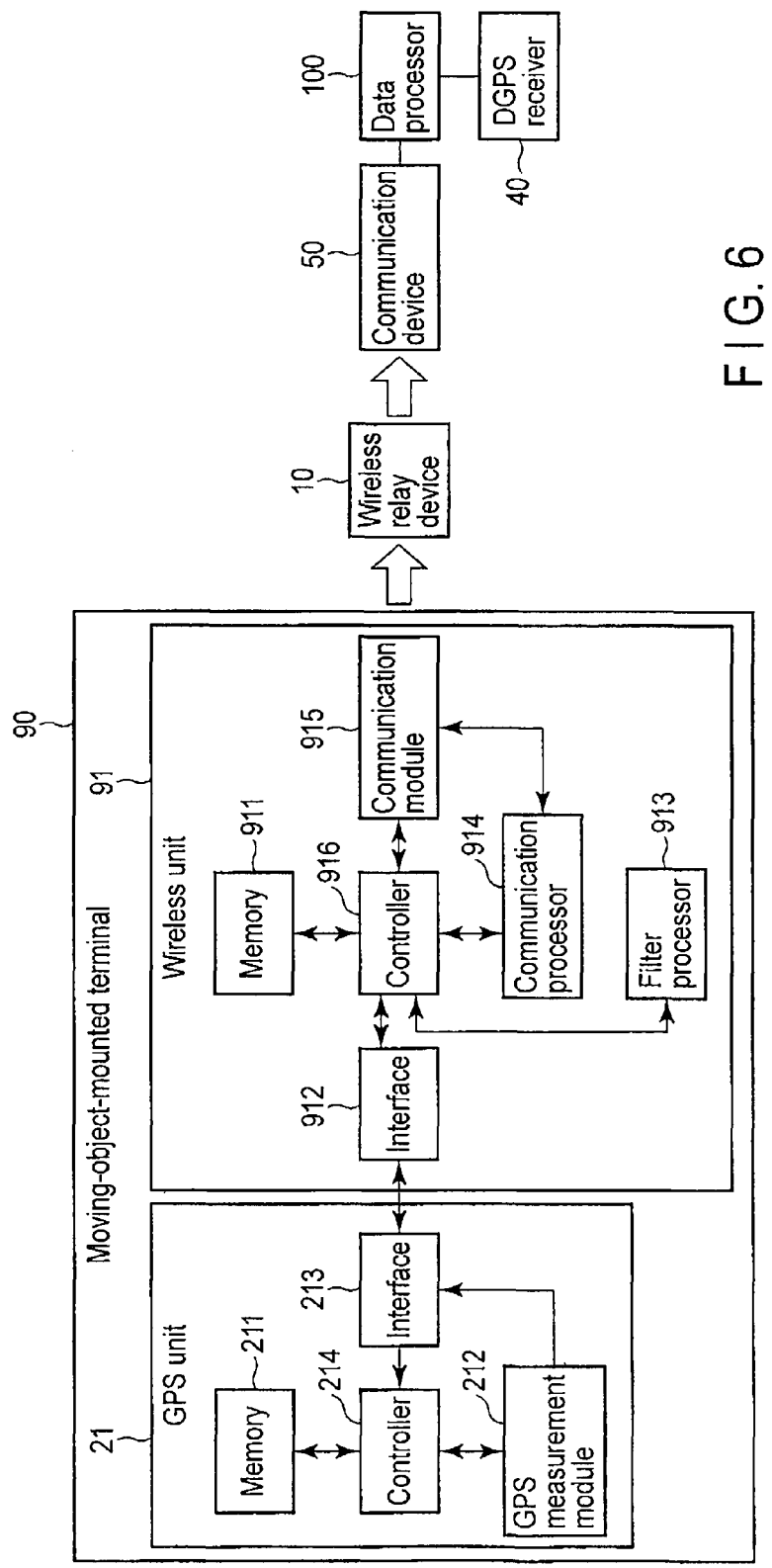
FIG. 6 is an exemplary block diagram showing a configuration of a measurement system according to the second embodiment.

FIG. 6 is a block diagram showing a configuration of a measurement system according to the second embodiment. In FIG. 6, units specified by the same reference number as FIG. 1 carry out the same operation.

The measurement system shown in FIG. 6 includes a wireless relay device 10, a moving-object-mounted terminal 90, a data processor 100, a DGPS receiver 40 and a communication device 50.

The moving-object-mounted terminal 90 includes a GPS unit 21 and a wireless unit 91.

The GPS unit 21 includes a memory 211, a GPS measurement module 212, an interface 213 and a controller 214.

The controller 214 provides an instruction to the GPS measurement module 212 to acquire positional data of a moving object in accordance with one of a first and second acquisition frequencies f1, f2 stored in the memory 211 on the basis of a frequency control signal output from the wireless unit 91.

The wireless unit 91 includes a memory 911, an interface 912, a filter processor 913, a communication processor 914, a communication module 915 and a controller 916.

The memory 911 stores an ID number assigned to the moving-object-mounted terminal 90 beforehand. The memory 911 also stores area data of a measurement area and individual information of the moving object beforehand. The individual information includes the name of horse, and a unique number assigned for each racehorse, for example. The memory 911 pre-stores the precise measurement starting velocity $V_{s1}$, the precise measurement ending velocity $V_{e1}$, the communication starting velocity $V_{s0}$ and the communication ending velocity $V_{e0}$, where $V_{s1} > V_{e1} > V_{s0} > V_{e0}$.

The interface 912 receives the positional data and time data from the GPS unit 21. The interface 912 outputs a frequency control signal output from the controller 916 to the GPS unit 21.

The filter processor 913 performs filter processing on the time-sampled series of positional data. By this processing, the filter processor 913 calculates the positional data in which the observation error is reduced (hereinafter, referred to as smoothed position) and the smoothed rate of movement (hereinafter, referred to as smoothed velocity). The detailed filter processing is the same as that of the filter processor 32 of the first embodiment. The filter processor 913 outputs the calculated smoothed velocity and smoothed position to the controller 916.

The communication processor 914 receives the positional data and the time data from the GPS unit 21 and the ID number and the individual information from the memory 911, and modulates the received data according to the communication format. The communication processor 914 outputs the modulated signal to the communication module 915.

The communication processor 914 demodulates the wireless signal received at the communication module 915 according to the communication format. The communication processor 914 then outputs the demodulated signal to the controller 916.

The communication module 915 changes the frequency of the modulated signal received from the communication processor 914 to the frequency band for wireless communication, amplifies power, and externally transmits the modulated signal as a wireless signal. If the positional data and the time data are acquired at the first acquisition frequency f1, the communication module 915 may transmit the wireless signal in a transmit frequency which is less than or equal to f1. If the positional data and the time data are acquired at the second acquisition frequency f2, the communication module 224 may transmit the wireless signal in a transmit frequency which is less than or equal to f2. If the wireless signal is transmitted in the transmit frequency less than f1 or f2, the positional data and the time data are temporally stored in the memory 911.

The communication module 915 receives the externally transmitted wireless signal. The communication module 915 also transfers the frequency of the received wireless signal to an intermediate frequency band and outputs the signal to the communication processor 914.

The communication module 915 is turned on or off by the controller 916.

The controller 916 includes a CPU, for example, and has functions as shown in FIG. 7. The controller 916 includes a communication controller 9161, a frequency controller 9162, a velocity determination controller 9163 and an area determination controller 9164.

When the positional data and the time data are input from the GPS unit 21 to the communication controller 9161 via the interface 912, the communication controller 9161 reads the ID number and the individual information from the memory 911 and outputs the ID number and the individual information along with the positional data and the time data received from the GPS unit 21 to the communication processor 914.

The frequency controller 9162 reads the precise measurement starting velocity $V_{s1}$ and the precise measurement ending velocity $V_{e1}$ from the memory 911 upon reception of the smoothed velocity from the filter processor 913. The frequency controller 9162 compares the smoothed velocity received from the filter processor 913 with the precise measurement starting velocity $V_{s1}$ and the precise measurement ending velocity $V_{e1}$. If the smoothed velocity $>V_{s1}$, the frequency controller 9162 outputs a frequency control signal instructing execution of GPS measurement at the second acquisition frequency f2 to the GPS unit 21. If the smoothed velocity $<V_{e1}$, the frequency controller 9162 outputs a frequency control signal instructing execution of GPS measurement at the first acquisition frequency f1 to the GPS unit 21.

The velocity determination controller 9163 reads the communication starting velocity $V_{s0}$ and the communication ending velocity $V_{e0}$ from the memory 911 upon reception of the smoothed velocity from the filter processor 913. The velocity determination controller 9163 compares the smoothed velocity received from the filter processor 913 with the communication starting velocity $V_{s0}$ and the communication ending velocity $V_{e0}$. The velocity determination controller 9163 turns on the communication module 915 at the time when the smoothed velocity becomes larger than $V_{s0}$. The velocity determination controller 9163 turns off the communication module 915 at the time when the smoothed velocity becomes less than $V_{e0}$ while the communication is maintained.

The area determination controller 9164 compares the smoothed position received from the filter processor 913 with area data stored in the memory 911 and determines whether the moving object exists within the measurement area upon reception of the smoothed position. If the moving object does not exist within the measurement area, the area determination controller 9164 turns off the communication module 915 not to transmit or receive the wireless signal. If the moving object exists within the measurement area, the area determination controller 9164 turns on the communication module 915 to transmit or receive the wireless signal.

For example, the communication module 915 is turned on only if both of the velocity determination controller 9163 and the area determination controller 9164 instruct the communication module 915 to be turned on. This further reduces power requirements.

The data processor 100 shown in FIG. 6 receives DGPS data acquired by the DGPS receiver 40 and the demodulated signal from the communication device 50. The demodulated signal includes the positional data, time data, ID number and individual information. FIG. 8 is a block diagram showing the configuration of the data processor 100 according to the second embodiment. The data processor 100 show in FIG. 8 includes a DGPS measurement processor 101, a furlong time calculation processor 102, a ranking acquisition module 103 and a filter processor 104.

The DGPS measurement processor 101 performs DGPS processing by using the positional data and the time data included in the demodulated signal and the DGPS data received from the DGPS receiver 40. The DGPS processing is position correction processing which includes calculating an error component from the positional data received from the DGPS receiver 40 fixed to a predetermined position whose precise position is acquired, and eliminate the error component included in the positional data acquired from the moving-object-mounted terminal 90 based on the correlation between the positional data acquired from the fixed DGPS receiver and moving-object-mounted terminal 90. The observational error which is a random component is added on the positional data after the DGPS processing. The DGPS measurement processor 101 outputs the positional data subjected to the DGPS processing and the time data to the filter processor 104.

The filter processor 104 calculates the smoothed position and the smoothed velocity in which the observation error is decreased, and outputs the smoothed position, the smoothed velocity, and the time data to the furlong time calculation processor 102 and the ranking acquisition module 103. The calculation at the filter processor 104 is the same as that of the filter processor 32 according to the first embodiment.

The furlong time calculation processor 102 receives the smoothed velocity, smoothed position and time data from the filter processor 104. The received smoothed velocity, smoothed location and time data include the ID number and individual information. The furlong time calculation processor 102 calculates time when the moving object passes through the preset start position and finish position of each furlong on the basis of the smoothed velocity, smoothed position and time data, and calculates the time difference as a furlong time. The furlong time calculation processor 102 calculates furlong times for each moving object identified by the ID number, and outputs the calculated furlong times, the ID number and the individual information to the post-processing format.

The ranking acquisition module 103 receives the smoothed velocity, smoothed position and time data from the filter processor 104. The ranking acquisition module 103 acquires the ranking of moving objects at the time when they passed through the preset positions within the wireless area, on the basis of the smoothed velocity, smoothed position, time data and ID numbers. The ranking acquisition module 103 outputs the acquired ranking, ID numbers and individual information to the post-processing format.

For example, the post-processing format may be a display (not shown), and the furlong time and the ranking associated with the ID number and individual information may be shown on the display.

The operation of switching the acquiring frequencies by the GPS unit 21 in the above-mentioned measurement system will be described below in the details.

Figure 9:
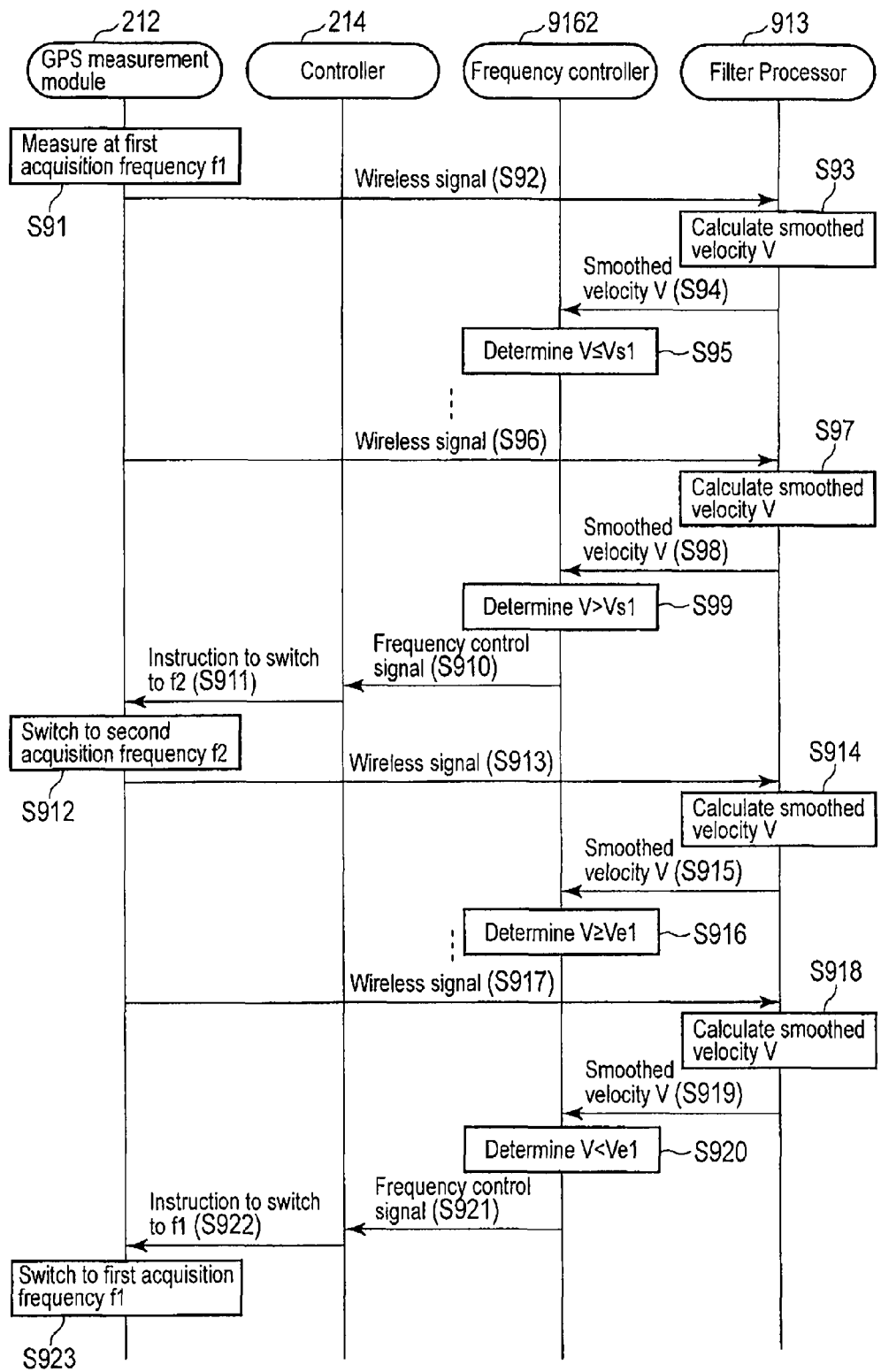
FIG. 9 illustrates the sequence of switching acquisition frequencies of the GPS measurement module of the measurement system shown in FIG. 6.

FIG. 9 illustrates an example sequence of switching acquisition frequencies by the GPS measurement module 212 of the measurement system according to the second embodiment.

The wireless area includes one or more measurement courses. If a racehorse enters the wireless area, wireless communication between the wireless unit 91 and wireless relay device 10 is established. At the time when the wireless communication is established, an instruction for initiating GPS measurement is provided to the GPS unit 21 so that the GPS measurement module 212 starts GPS measurement by the controller 916. The GPS measurement module 212 acquires the positional data and time data at the first acquisition frequency f1 (sequence S91). The acquired positional data and time data are output to the filter processor 913 via the controller 916 (sequence S92).

The filter processor 913 calculates the smoothed velocity V based on the positional data and time data (sequence S93). The filter processor 913 outputs the calculated smoothed velocity V to the frequency controller 9162 (sequence S94). The frequency controller 9162 compares the smoothed velocity V with the precise measurement starting velocity $V_{s1}$ and the precise measurement ending velocity $V_{e1}$ (sequence S95). The GPS unit 21 continuously acquires the positional data and time data at the first acquisition frequency f1 and outputs the acquired data to the filter processor 913 until the frequency controller 9162 determines that $V > V_{s1}$ (sequence S96).

If the smoothed velocity V becomes greater than $V_{s1}$ ($V > V_{s1}$) (sequences S97 to S99), the frequency controller 9162 outputs a frequency control signal instructing execution of GPS measurement at the second acquisition frequency f2 to the GPS unit 21 (sequence S910). The controller 214 reads the second acquisition frequency f2 from the memory 211 and controls the GPS measurement module 212 to initiate GPS measurement at the second acquisition frequency f2 upon reception of the frequency control signal from the frequency controller 9162 (sequence S911).

The GPS measurement module 212 performs the GPS measurement at the second acquisition frequency f2 and acquires the positional data and time data (sequence S912). The acquired positional data and time data are output to the filter processor 913 via the controller 916 (sequence S913).

The filter processor 913 calculates the smoothed velocity V based on the positional data and time data (sequence S914). The filter processor 913 outputs the calculated smoothed velocity V to the frequency controller 9162 (sequence S915). The frequency controller 9162 compares the smoothed velocity V with the precise measurement starting velocity $V_{s1}$ and the precise measurement ending velocity $V_{e1}$ (sequence S916). The GPS unit 21 continuously acquires the positional data and time data at the second acquisition frequency f2 and outputs the acquired data to the filter processor 913 until the frequency controller 9162 determines that $V < V_{e1}$ (sequence S917).

If the smoothed velocity V becomes less than $V_{e1}$ ($V < V_{e1}$) (sequences S918 to S920), the frequency controller 9162 outputs a frequency control signal instructing execution of GPS measurement at the first acquisition frequency f1 to the GPS unit 21 (sequence S921). The controller 214 reads the first acquisition frequency f1 from the memory 211 and controls the GPS measurement module 212 to initiate GPS measurement at the first acquisition frequency f1 upon reception of the frequency control signal from the frequency controller 9162 (sequence S922).

The GPS measurement module 212 performs the GPS measurement at the first acquisition frequency f1 and acquires the positional data and time data (sequence S923).

In the second embodiment, the wireless area including the measurement area is formed by the wireless relay device 10, and the moving-object-mounted terminal 90 transmits the positional data and time data acquired by the GPS measurement to the data processor 100 via the wireless LAN. Accordingly, it is possible not to frighten racehorses without a large-sized gate and to realize transmission of the positional data and time data of racehorses to the data processor 100.

According to the second embodiment, the frequency of GPS measurement by the GPS unit 21 is changed in accordance with the smoothed velocity of a racehorse calculated at the wireless unit 91. This accomplishes high-precision furlong time measurement by increasing the acquisition frequency when a racehorse moves at high velocity (greater than or equal to $V_{s1}$).

According to the second embodiment, the communication module 915 is turned on or off in accordance with the smoothed velocity calculated at the wireless unit 91. Doing so, while a racehorse is not moving, a wireless signal is not transmitted or received. Accordingly, power requirement within the system can be reduced.

According to the second embodiment, the wireless unit 91 performs the filter processing relative to the positional data and time data received from the GPS unit 21. This realizes calculation of the smoothed velocity and smoothed position even if the GPS measurement is performed in the different acquisition frequencies. In addition, the smoothed velocity and smoothed position can be calculated even if the GPS data cannot be continuously received due to the low data communication quality in the wireless LAN communication.

According to the second embodiment, if a position indicated by the positional data acquired by the GPS measurement is not included in the measurement area defined by the pre-stored area data, the communication module 915 is turned off by the area determination controller 9164, thus reducing power requirements. In addition, if the position indicated by the positional data acquired by the GPS measurement is not include in the measurement area defined by the pre-stored area data, the frequency control signal output from the controller 916 of the wireless unit 91 is set to fix the frequency of GPS measurement to £1 regardless of the smoothed velocity. This also reduces power requirements.

According to the second embodiment, the ID numbers are pre-stored in the memory 911 of the wireless unit 91, thereby identifying each of the plurality of moving-object-mounted terminals 90 in the wireless area.

According to the second embodiment, the individual information of each moving object is pre-stored in the memory 911 of the wireless unit 91, thereby displaying the individual information of each racehorse associated with the calculated furlong times.

As stated above, with the measurement system according to the second embodiment, the furlong time of a racehorse galloping at high velocity can be automatically and surely obtained so that racehorses are not aware of the system even without the presence of a large-sized gate.

The configuration of the measurement system according to the second embodiment may not be limited to the configuration shown in FIG. 6. For example, as shown in FIG. 10, the measurement system may further include a vibration-type generator 60, a heart rate measurement device 70 and a data acquisition device 80, as shown in FIG. 5 of the first embodiment.

The second embodiment illustrates an example case where the memory 211 of the GPS unit pre-stores the first acquisition frequency f1 and the second acquisition frequency f2 (f1<f2), and the memory 911 of the wireless unit 91 pre-stores the precise measurement starting velocity $V_{s1}$, the precise measurement ending velocity $V_{e1}$, the communication starting velocity $V_{s0}$ and the communication ending velocity $V_{e0}$ ($V_{s1}>V_{e1}>V_{s0}>V_e$). In such a case, the frequency of GPS measurement is controlled by the frequency controller 9162 in accordance with the smoothed velocity of the moving object, and the communication module 915 is turned on or off by the velocity determination controller 9163. However, the frequency of GPS measurement and the transmission of wireless signal may be controlled in the other way. For example, the memory 211 may pre-store the zero to second acquisition frequencies f0 to f2 (f0<f1<f2), and the moving-object-mounted terminal 90 may operate as shown in FIG. 11 by being controlled by the frequency controller 9162 and the velocity determination controller 9163.

That is, the frequency controller 9162 reads the communication starting velocity $V_{s0}$ and the precise measurement starting velocity $V_{s1}$ from the memory 911 upon reception of the smoothed velocity from the filter processor 913. The frequency controller 9162 compares the smoothed velocity received from the filter processor 913 with the communication starting velocity $V_{s0}$ and the precise measurement starting velocity $V_{s1}$. If the smoothed velocity $\leq V_{s0}$, the frequency controller 9162 outputs a frequency control signal instructing execution of GPS measurement in the zero acquisition frequency f0 to the GPS unit 21. If $V_{s0}$<the smoothed velocity $\leq V_{s1}$, the frequency controller 9162 outputs a frequency control signal instructing execution of GPS measurement at the first acquisition frequency f1 to the GPS unit 21. If the smoothed velocity $>V_{s1}$, the frequency controller 9162 outputs a frequency control signal instructing execution of GPS measurement at the second acquisition frequency f2 to the GPS unit 21. The velocity determination controller 9163 reads the communication starting velocity $V_{s0}$ from the memory 911 upon reception of the smoothed velocity from the filter processor 913. The velocity determination controller 9163 compares the smoothed velocity received from the filter processor 913 with the communication starting velocity $V_{s0}$. The velocity determination controller 9163 turns on the communication module 915 to transmit a wireless signal at the time when the smoothed velocity becomes larger than $V_{s0}$ (the smoothed velocity $>V_{s0}$).

The second embodiment illustrates an example that the smoothed velocity and smoothed position calculated at the filter processor 913 is output to the controller 916. However, the smoothed velocity and smoothed position may be output in the other way. For example the moving-object-mounted terminal 90 may output the smoothed velocity and smoothed position calculated at the filter processor 913 and the time data received from the GPS unit 21 as a wireless signal via the communication processor 914 and the communication module 915. This eliminates the necessity of filter processing of the data processor 100. However, this processing may be adopted mainly for a system which can obtain positional data accurately even without performing the DGPS processing since an error may be large if the smoothed position is corrected by the DGPS processing. In such a case, the data processor 100 does not need the DGPS measurement processor. The measurement system which excludes the filter processing and DGPS processing is shown in FIG. 12, and the data processor 100 of such a measurement system is shown in FIG. 13.

In the second embodiment, the frequency controller 9162 compares the smoothed velocity received from the filter processor 913 with the precise measurement starting velocity $V_{s1}$ and the precise measurement ending velocity $V_{e1}$, and outputs a frequency control signal to switch the first and second acquisition frequencies f1 and f2 to the GPS unit 21. However, the frequency control signal to switch the first and second acquisition frequencies f1 and f2 may be output in other ways. For example, the frequency controller 9162 may output the frequency control signal to switch the first and second acquisition frequencies f1 and f2 to the GPS unit 21 on the basis of the smoothed position received from the filter processor 913. If the frequency controller 9162 has both of the function of performing acquisition frequency control by velocity and the function of performing acquisition frequency control by position, the precise measurement may be initiated only if the smoothed velocity exceeds the precise measurement starting velocity $V_{s1}$, and the smoothed position indicates a position within a predetermined area, for example.

If the frequency controller 9162 outputs the frequency control signal to switch the first and second acquisition frequencies f1 and f2 to the GPS unit 21 on the basis of the smoothed position, the frequency controller 9162 performs, for example, first or second processing described below.

Below are operations included in the first processing. The frequency controller 9162 compares the smoothed position received from the filter processor 913 with the area data stored in the memory 911 and determines whether the moving object is within the measurement area upon reception of the smoothed position. If the smoothed position is not within the area defined by the area data, the frequency controller 9162 outputs a frequency control signal indicating execution of GPS measurement at the first acquisition frequency f1 to the GPS unit 21. If the smoothed positions within the area defined by the area data, the frequency controller 9162 outputs a frequency control signal indicating execution of GPS measurement at the second acquisition frequency f2 to the GPS unit 21.

Below are operations included in the second processing. The memory 911 pre-stores first and second area data. The first area data is used for turning on or off the communication module 915 by the area determination controller 9164. The second area data refers to a part of the first area data. The frequency controller 9162 compares the smoothed position received from the filter processor 913 with the second area data stored in the memory 911 and determines whether the moving object is within the area defined by the second area data upon reception of the smoothed position. If the smoothed position is not within the area defined by the second area data, the frequency controller 9162 outputs a frequency control signal indicating execution of GPS measurement at the first acquisition frequency f1 to the GPS unit 21. If the smoothed position is within the area defined by the second area data, the frequency controller 9162 outputs a frequency control signal indicating execution of GPS measurement at the second acquisition frequency f2 to the GPS unit 21.

Other Embodiments

The above embodiments explain the cases where the ID number is pre-stored in the memory 221, 911 of the wireless unit 22, 91, but is not limited thereto. For example, the ID number may be pre-stored in the memory 211 of the GPS unit, and output to the wireless unit 22, 91 along with the positional data and time data.

The above embodiments explain the cases where the individual information is pre-stored in the memory 221, 911 of the wireless unit 22, 91, but is not limited thereto. The individual information may be stored in the data processor 30, 100 as a database associated with the ID numbers. In such a case, data can be updated at a time by updating the data base of the data processor even if data is not updated to the moving-object-mounted terminals mounted on each individual racehorse.

The above embodiments explain the cases where the DGPS measurement processor 31, 101 performs the DGPS processing. However, it may not be necessary to provide the DGPS receiver 40.

The above embodiments explain the cases where the precise measurement starting velocity $V_{s1}$, the precise measurement ending velocity $V_{e1}$, the communication starting velocity $V_{s0}$ and the communication ending velocity $V_{e0}$ are pre-stored and compared with the smoothed velocity V. However, the precise measurement starting velocity $V_{s1}$, the precise measurement ending velocity $V_{e1}$ may be set as the precise measurement threshold velocity $V_{sh1}$. In such a case, the determination module 33 or the frequency controller 9162 determines whether or not to switch the acquisition frequency based on whether or not the smoothed velocity exceeds the precise measurement threshold velocity $V_{sh1}$. In addition, the communication starting velocity $V_{s0}$ and the communication ending velocity $V_{e0}$ may be set as the precise measurement threshold velocity $V_{sh0}$. In such a case, the velocity determination controller 9163 turns on or off the communication module 915 based on whether or not the smoothed velocity exceeds the precise measurement threshold velocity $V_{sh0}$.

The above embodiments explain the cases where the GPS measurement is initiated when a racehorse enters the wireless area. However, the trigger of initiating the GPS measurement is not limited thereto. For example, an acceleration sensor is mounted in the wireless unit 22, 91, and the GPS measurement is initiated when vibration is detected by the sensor. If vibration is not detected for a certain time, the GPS measurement may not be performed. In such a case, initiation of the GPS measurement and turning on the communication module 915 can be controlled at a time, and therefore further reducing power requirement.

The above embodiments explain the cases where the GPS measurement module 212 acquires positional data and time data. However, the GPS measurement module 212 may calculate velocity data by Doppler frequency of satellite radio waves received from multiple satellites. In addition, the GPS measurement module 212 may calculate velocity data by acquired positional data and time data. In such a case, the controller 225, 916 compares the velocity data pre-stored in the memory 211, 911 with the velocity data received from the GPS measurement module 212, and controls the acquisition frequency of the GPS unit 21 by the frequency controller 2252, 9162. In addition, the controller 225 further includes the velocity determination controller 2254. The controller 225, 916 compares the velocity data pre-stored in the memory 221, 911 with the velocity data received from the GPS measurement module 212, and turns on or off the communication module 224, 915 by the velocity determination controller 2254, 9163.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A measurement system comprising:
   a wireless relay device forming a wireless area for performing wireless communication;
   a moving-object-mounted terminal mounted to a moving object within the wireless area, the moving-object-mounted terminal comprising:
   a Global Positioning System (GPS) unit configured to acquire positional data of the moving object and time data indicating a time when the positional data has been acquired by the GPS unit; and a wireless unit configured to convert the positional data and the time data into a wireless signal and to transmit the wireless signal to the wireless relay device; and a data processor configured to receive the wireless signal from the moving-object-mounted terminal via the wireless relay device, and to calculate a time required for the moving object to move a predetermined distance within the wireless area, based on the positional data and the time data, wherein the data processor comprises:

a filter processor configured to calculate a smoothed velocity by performing a filter processing on the positional data and the time data; and a determination module configured to transmit a precise measurement starting signal to the wireless relay device if the smoothed velocity becomes larger than a predetermined first velocity, and to transmit a precise measurement ending signal to the wireless relay device if the smoothed velocity becomes less than a predetermined second velocity;

the GPS unit comprises:

a memory configured to pre-store a first acquisition frequency and a second acquisition frequency which is higher than the first acquisition frequency; and a GPS measurement module configured to select one of the first and second acquisition frequencies and to acquire the positional data and the time data at the selected acquisition frequency; and the wireless unit comprises:

a frequency controller configured to instruct the GPS unit to select the second acquisition frequency if the precise measurement starting signal is received via the wireless relay device, and to instruct the GPS unit to select the first acquisition frequency if the precise measurement ending signal is received via the wireless relay device.

2. The measurement system of claim 1, further comprising a Differential GPS (DGPS) receiver configured to acquire DGPS data, the data processor being configured to perform a correction of the positional data by using the DGPS data.

3. The measurement system of claim 1, further comprising a vibration-type generator configured to convert mechanical energy obtained by vibration because of a movement of the moving object into electrical energy, the GPS unit and the wireless unit being configured to be driven by the electrical energy.

4. The measurement system of claim 1, further comprising a heart rate measurement device configured to measure a heart rate of the moving object, if the moving object is an animal, the wireless unit being configured to convert the heart rate measured by the heart rate measurement device into a wireless signal along with the positional data and the time data.

5. The measurement system of claim 1, further comprising a data acquisition device configured to acquire various data regarding the moving object, the wireless unit being configured to convert the acquired various data into a wireless signal along with the positional data and the time data.

6. The measurement system of claim 1, wherein the wireless unit further comprises an area determination controller configured to determine whether the moving object exists within a predetermined area based on the positional data, to turn on the transmitting of the wireless signal to the wireless relay device if the moving object exists within the predetermined area, and to turn off the transmitting of the wireless signal to the wireless relay device if the moving object exists outside the predetermined area.

7. The measurement system of claim 1, wherein:

the GPS measurement module is configured to acquire velocity of the moving object by the GPS unit; and the wireless unit further comprises a velocity determination controller configured to turn on the transmitting of the wireless signal to the wireless relay device if the acquired velocity becomes larger than a predetermined communication starting velocity, and to turn off the transmitting of the wireless signal to the wireless relay device if the acquired velocity becomes less than a predetermined communication ending velocity.

8. The measurement system of claim 1, wherein the predetermined first velocity is equal to the predetermined second velocity.

9. A moving-object-mounted terminal for use in a measurement system configured to measure a time required for a moving object within a wireless area formed by a wireless relay device to move a predetermined distance, and mounted on the moving object, the moving-object-mounted terminal comprising:

a Global Positioning System (GPS) unit configured to acquire positional data of the moving object and time data indicating a time when the positional data has been acquired by the GPS unit; and a wireless unit configured to convert the positional data and the time data into a wireless signal and to transmit the wireless signal to the wireless relay device, wherein the wireless unit comprises:

an interface configured to receive the positional data and the time data from the GPS unit;

a communication processor configured to convert the received positional data and time data into a modulated signal in accordance with a predetermined communication format; and a communication module configured to transmit the modulated signal to the wireless relay device as the wireless signal;

the GPS unit comprises:

a memory configured to pre-store a first acquisition frequency and a second acquisition frequency which is higher than the first acquisition frequency; and a GPS measurement module configured to select one of the first and second acquisition frequencies and to acquire the positional data and the time data at the selected acquisition frequency by the GPS unit; and the wireless unit comprises:

a filter processor configured to perform a filter processing on the positional data and the time data received from the GPS unit, and to calculate a smoothed velocity of the moving object; and a frequency controller configured to instruct the GPS unit to select the second acquisition frequency if the smoothed velocity becomes larger than a predetermined first velocity, and to instruct the GPS unit to select the first acquisition frequency if the smoothed velocity becomes less than a predetermined second velocity.

10. The moving-object-mounted terminal of claim 9, wherein the wireless unit further comprises a velocity determination controller configured to turn on the communication module if the smoothed velocity becomes larger than a predetermined communication starting velocity, and to turn off the communication module if the smoothed velocity becomes less than a predetermined communication ending velocity.

11. The moving-object-mounted terminal of claim 10, wherein the predetermined communication starting velocity is equal to the predetermined communication ending velocity.

12. The moving-object-mounted terminal of claim 9, wherein:

the GPS measurement module is configured to further acquire velocity of the moving object by the GPS unit; and the wireless unit further comprises a velocity determination controller configured to turn on the communication module if the acquired velocity becomes larger than a predetermined communication starting velocity, and to turn off the communication module if the acquired velocity becomes less than a predetermined communication ending velocity.

13. The moving-object-mounted terminal of claim 9, wherein:

the filter processor is configured to perform the filter processing on the positional data and the time data received from the GPS unit and to calculate the smoothed position of the moving object; and the wireless unit further comprises an area determination controller configured to determine whether the moving object exists within a predetermined area based on the smoothed position, to turn on the communication module if the moving object exists within the predetermined area, and to turn off the communication module if the moving object exists outside the predetermined area.

14. The moving-object-mounted terminal of claim 9, wherein:

the filter processor is configured to perform the filter processing on the positional data and the time data received from the GPS unit and to calculate a smoothed position of the moving object; and the communication processor is configured to modulate the smoothed position, the smoothed velocity and the time data into a modulated signal in accordance with a predetermined communication format.

15. The moving-object-mounted terminal of claim 9, wherein:

the GPS unit is assigned an identification (ID) number used for identifying the moving-object-mounted terminal;

the GPS unit is configured to output the ID number along with the acquired positional data and time data to the wireless unit; and the wireless unit is configured to convert the ID number into a wireless signal in addition to the positional data and time data.

16. The moving-object-mounted terminal of claim 9, wherein:

the wireless unit is assigned an ID number used for identifying the moving-object-mounted terminal; and the wireless unit is configured to convert the ID number into a wireless signal in addition to the positional data and time data.

17. The moving-object-mounted terminal of claim 9, wherein:

the wireless unit is configured to pre-store individual information including a name of moving object and a unique number assigned to each moving object; and the wireless unit is configured to convert the individual information into a wireless signal in addition to the positional data and time data.

18. The moving-object-mounted terminal of claim 9, wherein the predetermined first velocity is equal to the predetermined second velocity.

19. The moving-object-mounted terminal of claim 9, further comprising a vibration-type generator configured to convert mechanical energy obtained by vibration because of a movement of the moving object into electrical energy, the GPS unit and the wireless unit being configured to be driven by the electrical energy.

20. The moving-object-mounted terminal of claim 9, further comprising a heart rate measurement device configured to measure a heart rate of the moving object, if the moving object is an animal, the wireless unit being configured to convert the heart rate measured by the heart rate measurement device into a wireless signal along with the positional data and the time data.

21. The moving-object-mounted terminal of claim 9, further comprising a data acquisition device configured to acquire various data regarding the moving object, the wireless unit being configured to convert the acquired various data into a wireless signal along with the positional data and the time data.

22. A moving-object-mounted terminal for use in a measurement system configured to measure a time required for a moving object within a wireless area formed by a wireless relay device to move a predetermined distance, and mounted on the moving object, the moving-object-mounted terminal comprising:

a Global Positioning System (GPS) unit configured to acquire positional data of the moving object and time data indicating a time when the positional data has been acquired by the GPS unit; and a wireless unit configured to convert the positional data and the time data into a wireless signal and to transmit the wireless signal to the wireless relay device wherein the wireless unit comprises:

an interface configured to receive the positional data and the time data from the GPS unit;

a communication processor configured to convert the received positional data and time data into a modulated signal in accordance with a predetermined communication format; and a communication module configured to transmit the modulated signal to the wireless relay device as the wireless signal;

the GPS unit comprises:

a memory configured to pre-store a first acquisition frequency and a second acquisition frequency which is higher than the first acquisition frequency; and a GPS measurement module configured to select one of the first and second acquisition frequencies and to acquire the positional data and the time data at the selected acquisition frequency by the GPS unit; and the wireless unit comprises:

a filter processor configured to perform a filter processing on the positional data and the time data received from the GPS unit and to calculate a smoothed position of the moving object; and a frequency controller configured to determine whether the moving object exists within a predetermined area, to instruct the GPS unit to select the second acquisition frequency if the moving object exists within the predetermined area, and to instruct the GPS unit to select the first acquisition frequency if the moving object exists outside the predetermined area.

23. The moving-object-mounted terminal of claim 22, wherein the filter processor is configured to perform the filter processing on the positional data and the time data received from the UPS unit and to calculate a smoothed velocity of the moving object, and the wireless unit further comprises a velocity determination controller configured to turn on the communication module if the smoothed velocity becomes larger than a predetermined communication starting velocity, and to turn off the communication module if the smoothed velocity becomes less than a predetermined communication ending velocity.

24. The moving-object-mounted terminal of claim 22, wherein:

the GPS measurement module is configured to further acquire velocity of the moving object by the GPS unit; and the wireless unit further comprises a velocity determination controller configured to turn on the communication module if the acquired velocity becomes larger than a predetermined communication starting velocity, and to turn off the communication module if the acquired velocity becomes less than a predetermined communication ending velocity.

25. The moving-object-mounted terminal of claim 22, wherein the wireless unit further comprises an area determination controller configured to determine whether the moving object exists within a predetermined area based on the smoothed position, to turn on the communication module if the moving object exists within the predetermined area, and to turn off the communication module if the moving object exists outside the predetermined area.

26. The moving-object-mounted terminal of claim 22, wherein:

the filter processor is configured to perform the filter processing on the positional data and the time data received from the GPS unit and to calculate a smoothed velocity of the moving object; and the communication processor is configured to modulate the smoothed position, the smoothed velocity and the time data into a modulated signal in accordance with a predetermined communication format.

27. The moving-object-mounted terminal of claim 22, wherein:

the GPS unit is assigned an identification (ID) number used for identifying the moving-object-mounted terminal;

the GPS unit is configured to output the ID number along with the acquired positional data and time data to the wireless unit; and the wireless unit is configured to convert the ID number into a wireless signal in addition to the positional data and time data.

28. The moving-object-mounted terminal of claim 22, wherein:

the wireless unit is assigned an ID number used for identifying the moving-object-mounted terminal; and the wireless unit is configured to convert the ID number into a wireless signal in addition to the positional data and time data.

29. The moving-object-mounted terminal of claim 22, further comprising a vibration-type generator configured to convert mechanical energy obtained by vibration because of a movement of the moving object into electrical energy, the GPS unit and the wireless unit being configured to be driven by the electrical energy.

30. The moving-object-mounted terminal of claim 22, further comprising a heart rate measurement device configured to measure a heart rate of the moving object, if the moving object is an animal, the wireless unit being configured to convert the heart rate measured by the heart rate measurement device into a wireless signal along with the positional data and the time data.

31. The moving-object-mounted terminal of claim 22, further comprising a data acquisition device configured to acquire various data regarding the moving object, the wireless unit being configured to convert the acquired various data into a wireless signal along with the positional data and the time data.

32. A data processor for use in a measurement system configured to acquire positional data of a moving object within a wireless area formed by a wireless relay device and time data indicating a time when the positional data has been acquired by a GPS processing of a moving-object-mounted terminal mounted on the moving object, the data processor comprising:

a filter processor configured to receive the positional data and the time data acquired at the moving-object-mounted terminal via the wireless relay device, and to calculate a smoothed position and a smoothed velocity of the moving object by performing a filter processing on the positional data and the time data;

a first calculation processor configured to calculate a time required for the moving object to move a predetermined distance within the wireless area, based on the smoothed position, the smoothed velocity and the time data; and a determination module configured to transmit a precise measurement starting signal instructing starting of a precise measurement to the moving-object-mounted terminal via the wireless relay device if the smoothed velocity received from the filter processor becomes larger than a predetermined first velocity, and to transmit a precise measurement ending signal instructing ending of a precise measurement to the moving-object-mounted terminal via the wireless relay device if the smoothed velocity becomes less than a predetermined second velocity.

33. The data processor of claim 32, further comprising a DGPS measurement processor configured to correct the positional data received from the moving-object-mounted terminal by using Differential GPS (DGPS) data acquired by a DGPS receiver.

34. The data processor of claim 32, further comprising a second calculation processor configured to, if a plurality of moving objects exist within the wireless area, and each moving-object-mounted terminal is assigned an ID number, determine a ranking of a plurality of moving objects at a time when the moving objects passed through a predetermined position within the wireless area, based on the smoothed position, the smoothed velocity, the time data and the ID number.

35. The data processor of claim 30, further comprising a data base configured to, if the moving-object-mounted terminal is assigned an ID number, pre-store individual information including a name of moving object and a unique number assigned to each moving object associated with the ID number, and if the ID number is received along with the positional data and the time data, to output the individual information corresponding to the received ID number.

36. The data processor of claim 32, wherein the predetermined first velocity is equal to the predetermined second velocity.

37. A data processor for use in a measurement system configured to acquire positional data of a moving object within a wireless area formed by a wireless relay device and time data indicating a time when the positional data has been acquired by a GPS processing of a moving-object-mounted terminal mounted on the moving object, the data processor comprising:
- a filter processor configured to receive the positional data and the time data acquired at the moving-object-mounted terminal via the wireless relay device, and to calculate a smoothed position and a smoothed velocity of the moving object by performing a filter processing on the positional data and the time data;
- a first calculation processor configured to calculate a time required for the moving object to move a predetermined distance within the wireless area, based on the smoothed position, the smoothed velocity and the time data; and
- a determination module configured to transmit a precise measurement starting signal instructing starting of a precise measurement to the moving-object-mounted terminal via the wireless relay device if the smoothed position received from the filter processor exists within a predetermined area, and to transmit a precise measurement ending signal instructing ending of a precise measurement to the moving-object-mounted terminal via the wireless relay device if the smoothed position exists outside the predetermined area.

38. A measurement system comprising:
a wireless relay device forming a wireless area for performing wireless communication;
a moving-object-mounted terminal mounted to a moving object within the wireless area, the moving-object-mounted terminal comprising:
- a Global Positioning System (GPS) unit configured to acquire positional data of the moving object and time data indicating a time when the positional data has been acquired by the GPS unit; and
- a wireless unit configured to convert the positional data and the time data into a wireless signal and to transmit the wireless signal to the wireless relay device; and a data processor configured to receive the wireless signal from the moving-object-mounted terminal via the wireless relay device, and to calculate a time required for the moving object to move a predetermined distance within the wireless area, based on the positional data and the time data, wherein the data processor comprises:
- a filter processor configured to calculate a smoothed position by performing a filter processing on the positional data and the time data; and
- a determination module configured to transmit a precise measurement starting signal to the wireless relay device if the smoothed position exists within a predetermined area, and to transmit a precise measurement ending signal to the wireless relay device if the smoothed position exists outside the predetermined area;

the GPS unit comprises:
- a memory configured to pre-store a first acquisition frequency and a second acquisition frequency which is higher than the first acquisition frequency; and
- a GPS measurement module configured to select one of the first and second acquisition frequencies and to acquire the positional data and the time data at the selected acquisition frequency; and the wireless unit comprises:
- a frequency controller configured to instruct the GPS unit to select the second acquisition frequency if the precise measurement starting signal is received via the wireless relay device, and to instruct the GPS unit to select the first acquisition frequency if the precise measurement ending signal is received via the wireless relay device.

* * * * *